United States Patent [19]
Sih

[11] Patent Number: 5,608,047
[45] Date of Patent: Mar. 4, 1997

[54] CYCLIC ADP-RIBOSE AND ANALOGS

[75] Inventor: Charles J. Sih, Madison, Wis.

[73] Assignee: Wisconsin Alumni Research Foundation, Madison, Wis.

[21] Appl. No.: 404,467

[22] Filed: Mar. 15, 1995

[51] Int. Cl.$^6$ .......................... C07H 19/167; C07H 19/20
[52] U.S. Cl. .................... 536/26.26; 536/26.23; 536/26.24
[58] Field of Search ................ 536/26.23, 26.24, 536/26.26, 55.3

[56] References Cited

PUBLICATIONS

Shinji Yamada et al, Cyclic ADP–Ribose Via Stereoselective Cyclization of β–NAD, 116, pp. 10787–10788, J. Am. Chem. So., 1994.

Qu–Ming Gu et al, Cyclic ADP–Ribose: Synthesis and Structural Assignment, 116, pp. 7481–7486, J. Am. Chem. Soc., 1994.

*Primary Examiner*—Gary L. Kunz
*Attorney, Agent, or Firm*—Andrus, Sceales, Starke & Sawall

[57] ABSTRACT

A non-enzymatic stereoselective cyclization of β-NAD$^+$ to yield cyclic ADP-ribose (cADPR). By heating β-NAD$^+$ in an anhydrous solvent in the presence of a metal halide and a nonnucleophilic base, cADPR was obtained as the sole cyclic isomer in yields as high as 28%. α-NAD was also converted into cADPR under the same reaction conditions.

Several analogs of cADPR have also been synthesized and some of these analogs have a greater Ca$^{++}$ release activity than cADPR itself.

3 Claims, 2 Drawing Sheets

EC50
Ins(1,4,5)P3 = 100nM
cATPR = 80nM
cADPR = 33μM cADPR = 40μM

CYCLIC ADP-RIBOSE AND ANALOGS

This invention was made with United States government support awarded by NIH Grant #R01 GM46290. The United States Government has certain rights in this invention.

BACKGROUND OF THE INVENTION

Many cellular functions are modulated by the concentration of intracellular calcium ions. Specifically, calcium ions act as intracellular messengers that regulate the functions of cells in many living systems. Two major receptor mechanisms of calcium mobilization are known that utilize calcium stored in cytoplasmic compartments for signaling. In epithelial and blood cells, the predominant mechanism of $Ca^{2+}$ release is triggered by the interaction of the second messenger, inositol 1,4,5-triphosphate ($IP_3$), with its receptor, a ligand-activated calcium-selective channel. The binding of $IP_3$ promotes channel opening, allowing $Ca^{2+}$ to flow into the cytoplasm.

A second class of intracellular calcium-releasing channels is the ryanodine receptor. These receptors are present in muscle and brain and may be activated by the plant alkaloid, ryanodine, and caffeine. Although the physiological activator of the ryanodine receptor is unknown, it can be activated by $Ca^{2+}$, causing the so called $Ca^{2+}$-induced $Ca^{2+}$ release (CICR). One ryanodine activator candidate is a metabolite of $\beta$-$NAD^+$, cyclic ADP-ribose (cADPR), which was shown to be as potent as $IP_3$ in mobilizing intracellular $Ca^{2+}$ stores in sea urchin eggs and in rat pituitary cells. cADPR has the following structure:

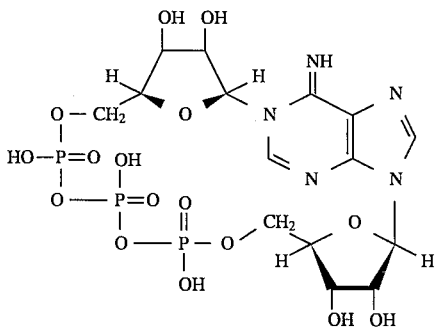

The widespread occurrence of the ryanodine receptor and cADPR in mammalian tissues suggests that cADPR may be an endogenous messenger for ryanodine receptors. Several other recent studies are consistent with this proposition.

Excitable Cell Pathways and Inexcitable Cell Pathways

Studies on calcium signaling have been divided into two separate categories: those focusing on electrically inexcitable cells, such as epithelial or blood, and those focusing on electrically excitable cells, such as nerve and muscle. However, both types of cells utilize calcium sequestered in cytosolic storage compartments for signaling, but excitable cells rely on a calcium-induced calcium release (CICR) mechanism, whereas for inexcitable cells the predominant mechanism for release is triggered by a diffusible second messenger, inositol 1,4,5-triphosphate ($IP_3$). Although signaling in both types of cells is influenced by plasma membrane calcium channels, the channels in the plasma membrane of inexcitable cells apparently are not regulated by membrane potential, as are excitable cells, and their pharmacology is different from that of the voltage-sensitive calcium channels of excitable cells.

In electrically inexcitable cells, signaling is generally initiated when an agonist activates a surface membrane receptor that, usually through a G protein, activates phospholipase C, which degrades phosphatidylinositol-4, 5diphosphate, releasing the soluble messenger, inositol-1,4, 5triphosphate ($IP_3$). The $IP_3$ activates an $IP_3$ receptor and thus releases calcium from an intracellular organelle to the cytoplasm. The release of calcium from the organelle causes a signal to be generated, which activates a plasma membrane calcium entry pathway (capacitative calcium entry). This signal may involve the release of another messenger, the calcium influx factor, when the intracellular stores of calcium are depleted.

In electrically excitable cells, patterns of calcium signaling are more variable. The $IP_3$-triggered mechanism, the CICR mode of signaling or a hybrid pathway may operate. However, in addition to, or instead of, the $IP_3$ receptor, many excitable cells express another intracellular calcium releasing channel: the ryanodine receptor. Calcium may enter cells when voltage-dependent calcium channels are activated by depolarization associated with action potentials. This calcium can cause further release of intracellularly stored calcium by activating the CICR mechanism associated with the ryanodine receptor calcium channel. This ryanodine receptor calcium channel may be regulated by cADPR. It increases the probability of channel opening of the ryanodine receptor by increasing its calcium sensitivity. By analogy with $IP_3$, there may be mechanisms regulating the cellular levels of cADPR.

These characteristics of excitable and inexcitable cells are not as separate as once thought. For example, earlier studies allowed for a ryanodine receptor-mediated CICR in inexcitable cells. It is now clear that the $IP_3$ receptor can also function as a CICR receptor. The current conjecture is that electrically inexcitable cells may contain only a single, homogeneous pool of intracellular calcium that is sensitive to $IP_3$, but electrically excitable cells may have a more complex arrangement of intracellular calcium pools regulated by different mechanisms, including cADPR.

Ryanodine Receptors and cADPR cADPR has no effects upon $IP_3$ receptors, but mounting evidence suggests that it is an endogenous activator of ryanodine receptor-mediated calcium release.

The ryanodine receptors are intracellular $Ca^{2+}$ release channels originally described in the sarcoplasmic reticulum of skeletal muscle (type 1, RYR1) or cardiac muscle (type 2, RYR2). They are named ryanodine receptors because they were first isolated based on their ability to bind ryanodine a plant alkaloid. Recently, a third type of ryanodine receptor (type 3, RYR3) was identified and was found to be widely distributed among tissues. There is now increasing evidence that cADPR activates the cardiac ryanodine receptor (RYR2) perhaps in an analogous way to the activation of the $IP_3$ receptors by $IP_3$.

cADPR has been shown to mobilize calcium by a mechanism independent of the IP$_3$ receptor, since its actions are not blocked by the IP$_3$ receptor antagonist heparin. The presence of ryanodine receptors in sea urchin eggs was first indicated by the existence of a 380 kDa protein which cross reacted with antibodies raised against the mammalian skeletal muscle. Based on cross desensitization studies and experiments with known ryanodine receptor antagonists, ryanodine, ruthenium red and procaine, cADPR was shown to release calcium via a ryanodine-sensitive CICR mechanism in sea urchin egg homogenates. Further, the ryanodine receptor activators, caffeine and divalent cations, potentiate cADPR but not IP$_3$-sensitive calcium release channels.

The Ca$^{2+}$ mobilizing action of cADPR is not confined to the sea urchin egg. cADPR has also been shown to mobilize calcium from permeabilized pituitary cells, dorsal root ganglion cells, pancreatic B-cells, brain microsomes, and heart sarcoplasmic reticulum vesicles, suggesting its widespread role in controlling calcium signals. Moreover, cADPR-induced calcium release from brain microsomes was blocked by ryanodine as was release from pancreatic β-cell microsomes and cardiac sarcoplasmic reticulum vesicles suggesting that cADPR, as in the sea urchin egg, was operating via a ryanodine receptor.

ADP Ribosyl Cyclase and the Prior Art cADPR is biosynthesized from NAD$^+$ by ADP-ribosyl cyclases (ADPR cyclases). These enzymes have been found in a variety of mammalian (rabbit heart, liver, brain, spleen and kidney, and in pituitary cells) and invertebrate tissues. Two types of the enzyme have been characterized: a 29 kDalton cytosolic form which has been purified, sequenced and cloned from the ovotestis of the sea hare, *Aplysia californica;* and a larger membrane-associated form (100 kDalton) found in mammalian cells. Endogenous levels of cADPR have been measured in a number of mammalian tissues including heart, liver, and brain. Basal levels of cADPR are typically in the range of 100–200 nM.

Specifically, ADPR-cyclase synthesizes cADPR from β-NAD$^+$. Structural evidence has been presented indicating that the metabolite is a cyclized ADP-ribose having an N-glycosyl linkage between the anomeric carbon of the terminal ribose unit and the N$^6$-amino group of the adenine moiety.

Prior to the present invention, synthesis of cADPR was only available through enzymatic means using ADPR-cyclases. A soluble form of the enzyme ADPR-cyclase has been purified and cloned from the ovotestis of the marine mollusk *Aplysia californica* but unfortunately, these systems are not accessible in quanities required for general use.

NAD$^+$ glycohydrolases (NADases), enzymes that are widely distributed among mammalian tissues, also catalyze the synthesis of cADPR from β-NAD$^+$. However, a problem with NADases is that the specific activities (nmol/mg of protein/h) of the NADases in most tissues are too low to be synthetically useful.

This lack of enzyme availability is a major problem with the enzymatic method of synthesizing cADPR. Another problem with using enzymes for synthesis of compounds is that enzymes must constantly be kept at optimal temperatures and only for short periods of time or else the enzymes will lose their activity. An additional problem encountered when using enzymes is that many enzymes require specific buffers to function in vitro.

SUMMARY OF THE INVENTION

A new chemical method for the synthesis of cADPR. The method utilizes the biomimetic cyclization of β-NAD$^+$. This invention is the first non-enzymatic stereoselective synthesis of cADPR from β-NAD$^+$. The cyclization is stereoselective as cADPR is obtained as a sole isomer.

The substrate specificity of this non-enzymatic intramolecular cyclization is comparable to that of the Aplysia enzyme, yet is readily available and is not plagued with the problems encountered using enzymes.

α-NAD$^+$ has also been subjected to the same reaction conditions. Again, cADPR was obtained as the only isomer, although the reaction rate was considerably slower than that of β-NAD$^+$.

In addition, this new cyclization procedure not only provides another alternative for the synthesis of cADPR, it also provides for the synthesis of cADPR analogs and affinity ligands for receptor protein(s) that are now only accessible by enzymatic means. The analogs of cADPR which have been synthesized using this novel chemical process prove to be a more potent activator of calcium release than cADPR itself.

BRIEF DESCRIPTION OF DRAWINGS

FIG. 1(*b*) shows the calcium releasing activity of cADPR in rat heart microsomes.

FIG. 1(*c*) illustrates the calcium releasing activity of cADPR in rat liver microsomes.

DETAILED DESCRIPTION OF THE PREFERRED EMBODIMENT

Figure 1A:
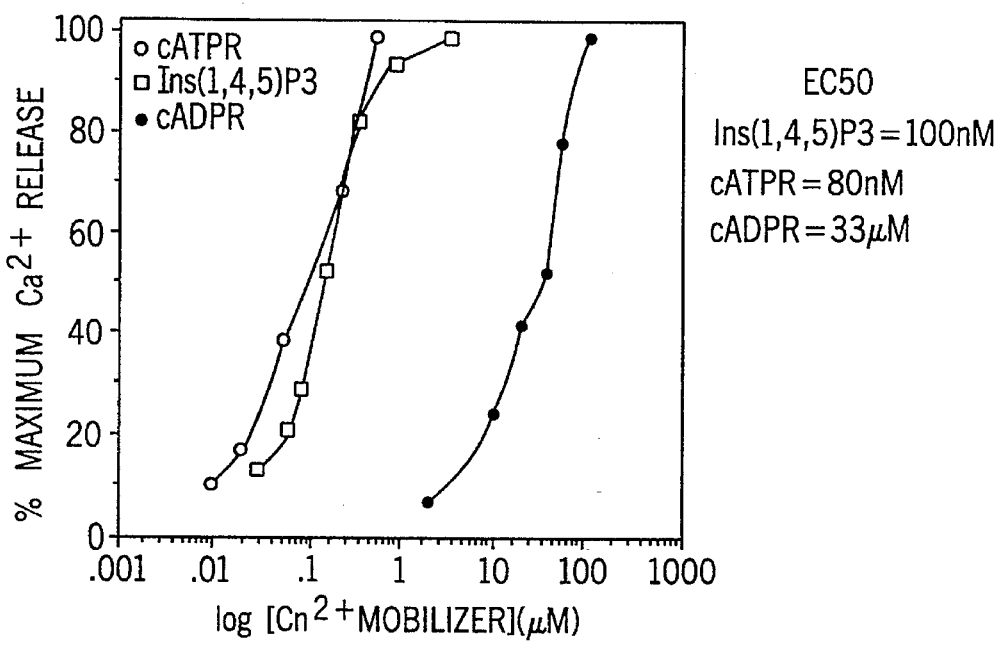
FIG. 1(*a*) shows the calcium releasing activity of cADPR as compared to cATPR and inositol 1,4,5-triphosphate in rat brain microsomes.
Figure 1B:
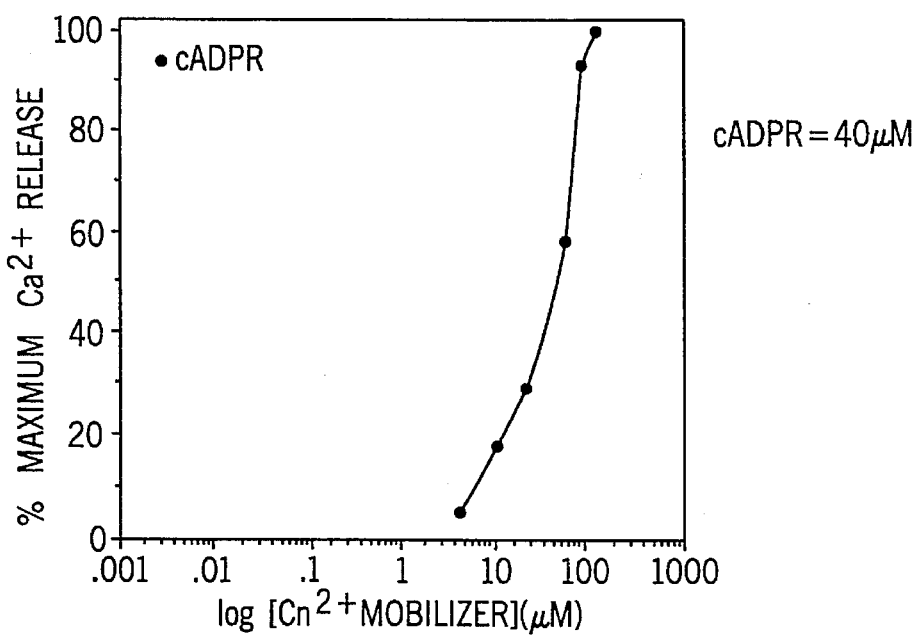
Figure 1C:
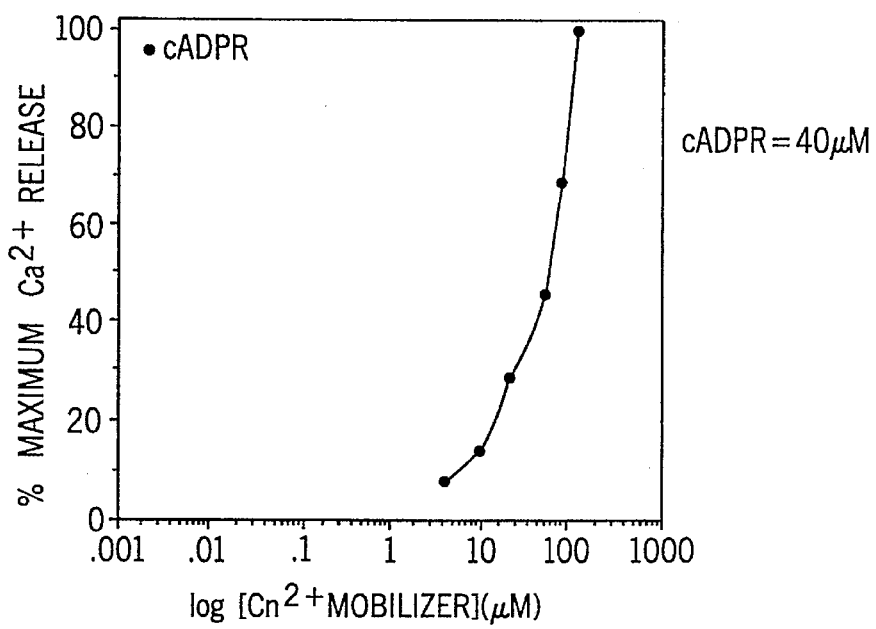

The biomimetic cyclization of β-NAD$^+$ is as follows:

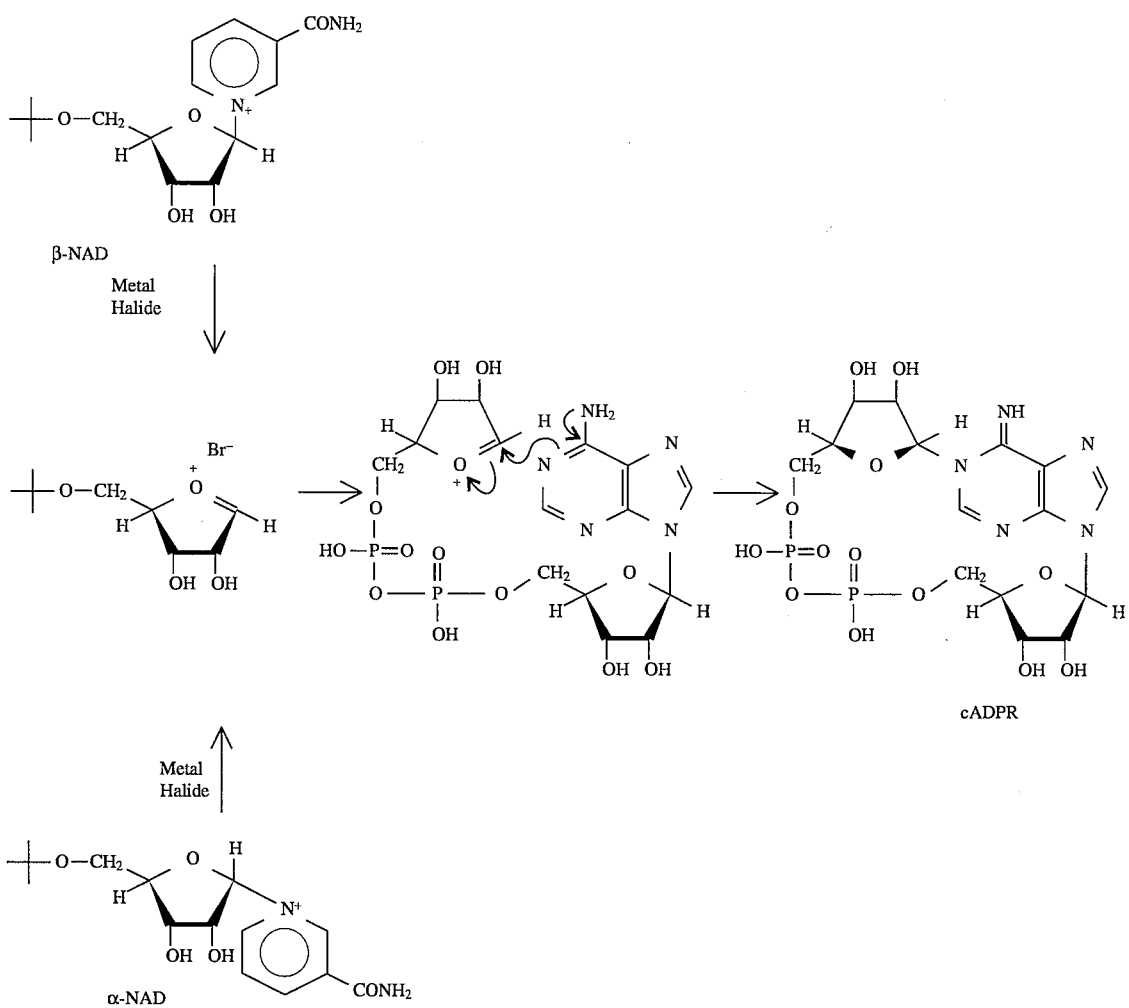

As the quaternary pyridinium group in β-NAD⁺ is a good leaving group, the cyclization of β-NAD⁺ was performed in different anhydrous solvents in the presence of nonnucleophilic bases and metal halides in order to exchange the quaternary pyridinium ion for a different leaving group. While there are no reports of nucleophilic substitutions of quaternary pyridinium groups by halides, the formation of a glycosyl halide may be possible using strong nucleophiles such as LiI.

EXAMPLE 1

By reacting β-NAD⁺ with LiI and trimethylamine in DMSO at 70° C., a small quantity of cADPR was formed. Other metal halides have been examined, and the best yield of cADPR was obtained with NaBr (28%) (see Table 1). Nicotinamide, remaining β-NAD⁺, and the side product, ADP-ribose (ADPR), were readily separated from cADPR by HPLC chromatography. More importantly, the cyclization was stereoselective, as cADPR was obtained as the sole isomer. As with most intramolecular cyclization reactions, the yield of cADPR decreased as the concentration of β-NAD⁺ increased.

TABLE 1

Effect of Metal Halides on the Cyclization of β-NAD⁺ [a]

| Reagents | β-NAD⁺(mM) | Time (h) | cADPR[b] (%) |
|---|---|---|---|
| LiBr | 1.5 | 2 | 2.1 |
| LiI | 1.5 | 2 | 0.5 |
| NaBr | 1.5 | 2 | 27.8 |
| NaBr | 7.5 | 2 | 14.8 |
| NaBr | 15.0 | 1 | 11.5 |
| NaI | 1.5 | 2 | 5.6 |
| KI | 1.5 | 2 | 4.2 |

Note:
[a] The reaction mixtures contained: metal halide, 747 mM; trethylamine, 1 μl/mg β-NAD⁺; in 5 ml of dry DMSO. After heating at 70° C. for 1–2 h, the DMSO was evaporated using a stream of nitrogen. The residue was dissolved in 100 μl of water and analyzed by anion exchange HPLC on a SynChropak AX100 column as described in the text.
[b] The yield of cADPR was calculated from the HPLC peak area using its molar extinction coefficient of 260 nm, pH 3.0 of 13,700. ¹H NMR (D₂O), d4.05–4.60 (9H, m), 5.39 (1H, t, J=5.62 Hz, $H_A2'$), 6.11 (1H, d, J=5.62 Hz, $H_A1'$), 6.20 (1H, d, J=7 Hz, H1'), 8.44 (1H, s, $H_A2$), and 9.05 (1H, s, $H_A8$).

A representative procedure for the preparation of cADPR is as follows: β-NAD⁺ (50 mg, 0.075 mmol) and NaBr (388 mg, 3.77 mmol), dried over P₂O₅ in a vacuum desiccator, were dissolved in 5 mL of fleshly distilled DMSO (dried by refluxing over CaH₂ for 14 h). To this solution was added triethylamine (25 μL), and the mixture was stirred at 70° C. for 1 h under an atmosphere of argon. After the solution was cooled, the products were precipitated by the addition of cold ethanol (25 mL). After drying, the residue was dissolved in 1 mL of H$_2$O, and the product was purified on a SynChropak AX-100 column (250×7.8 mm i.d., 5 μm) using a linear gradient of 0–1.05M NaCl in 0.1M KH$_2$PO$_4$ in 14 min. followed by an isocratic elution using 1.05M NaCl in 0.1M KH$_2$PO$_4$ for 20 min. at a flow rate of 1 mL/min. Fractions containing cADPR (retention time, 13.7 min.) were combined and further purified on a Waters Nova-Pak C$_{18}$ column (100×8 mm i.d., 4 μm). The column was eluted isocratically with 2 mM TFA at a flow rate of 1 mL/min. Evaporation of the solvent afforded 4.7 mg (11.5%) of cADPR, whose $^1$H NMR and mass spectra were found to be identical to those of the cADPR, prepared by enzymatic methods.

Ca$^{2+}$ release measurements as follows: Rat brain microsomes were prepared on the day of the experiment. Loading of the microsomes with Ca$^{2+}$ took approximately 30 minutes at 24° C. and was used at a protein concentration of 0.5 mg/ml. The free Ca$^{2+}$ used for Ca$^{2+}$ loading was 0.5 to 2 uM and was present in the loading solution as a contaminant. Ca$^{2+}$ uptake and release was followed by measuring extramicrosomal Ca$^{2+}$ using fluo-3 (Cal-Biochem) (1 uM). Fluorescence intensity of fluo-3 was measured at excitation and emission wavelength of 490 and 535 nm respectively. Fluorimetry was performed on 500 ul aliquots of microsomes using a Perkin Elmer MF-3. Additions were made in volumes of 1–5 ul and all chemicals were added in incubation medium containing 10 uM EGTA. Ca$^{2+}$ traces were calibrated by adding Ca$^{2+}$ standard solution. ADPR, β-NAD caused no Ca$^{2+}$ release and ryanodine inhibited release of Ca$^{2+}$ by cADPR but not that induced by IP$_3$. Conversely, heparin blocked Ca$^{2+}$ release induced by IP$_3$ but not by cADPR.

EXAMPLE 2

α-NAD$^+$ was subjected to the same reaction conditions. In this case, the reaction rate was found to be considerably slower than that of β-NAD$^+$ as manifested by the quantity of recovered α-NAD$^+$, but again, cADPR was obtained as the only isomer (see Table 2). These observations suggested that both cyclization reactions proceeded via a common oxocarbenium intermediate, similar to the proposed carbocation catalytic mechanism of phosphoribosyl transferases. However, at this stage we are uncertain as to whether a glycosyl halide is formed in the reaction.

TABLE 2

| | Cyclization of NAD Analogs | | | | |
|---|---|---|---|---|---|
| substrate (concn. mM) | NaBr (mM) | Et$_3$N (μL) | DMSO (mL) | time (h) | cyclized product (%) |
| β-NAD (14.9) | 747 | 50 | 5 | 2 | cADPR (27.8) |
| α-NAD (14.9) | 747 | 50 | 5 | 4 | cADPR (16.8) |
| NHD (14.9) | 742 | 20 | 2 | 2 | cHDPR (5.6) |
| NGD (14.9) | 742 | 20 | 2 | 2 | cGDPR (11.5) |
| 5'-TPM (11.5) | 636 | 50 | 3 | 2 | cATPR (10.0) |

NOTE: All reactions were conducted at 70° C. cADPR, cHDPR, and cATPR were isolated on a Synchropak AX-100 column (retention times were 13.7, 15.0, and 24.5–26 min. respectively) and were further purified on a C$_{18}$ column as described in the text. cGDPR was isolated directly on a Waters Nova-pak C$_{18}$ column, which was eluted isocratically with 2 mM TFA at a flow rate 1 mL/min. The retention time of cGDPR was 4.5 min.

EXAMPLE 3

Analogs to cADPR have also been synthesized using the novel chemical method. 5'-triphosphopyridine nucleotide (5'-TPN) was prepared in 70% yield by coupling β-nicotinamide mononucleotide (β-NMN) to ADP using 3-ethyl-1-(3-(dimethylamino)propyl)carbodiimide (EDC). When 5'-TPN was subjected to the same cyclization conditions as outlined in Example 1, cycle ATP-ribose (cATPR) (1) was isolated in about 10% yield. Its H NMR (D$_2$O) spectrum exhibited peaks at d 4.2–4.7 (9H, m), 5.36 (1H, t, J=5.0 Hz, H$_A$2'), 6.13 (1H, d, J=5.33 Hz. H$_A$1'), 6.23 (1H, d, J=4.3 Hz. H1'), 8.47 (1H, s, H$_A$2), and 9.11 (1H. s, H$_A$8), and its UV (A$_{260}$/A$_{290}$) ratio was similar to that cADPR at various pH values. These data are consistent for the expected cyclic structure having the glycosyl bond attached onto the N$^1$-nitrogen of the adenine ring.

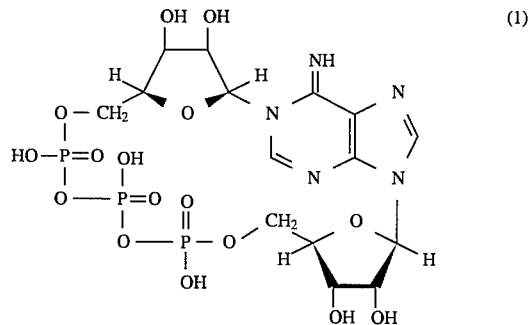

(1)

NAD analogs nicotinamide guanine dinucleotide (NGD) and nicotinamide hypoxanthine dinucleotide (NHD) have also been cyclized using the same reaction conditions. However, their $^1$H NMR and UV spectral data suggested that cyclization may have occurred with the N$^7$-nitrogen of the purine ring to furnish cGDPR (2) and cHDPR (3) in 11.5 and 5.6% yields, respectively. The structure of the analogs is as follows:

(2)

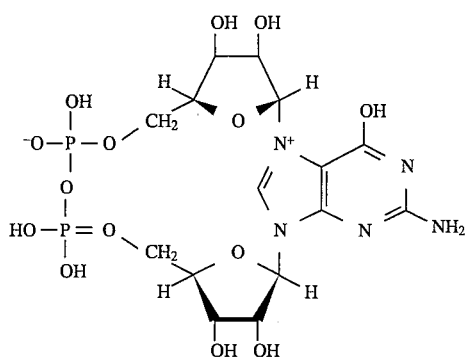

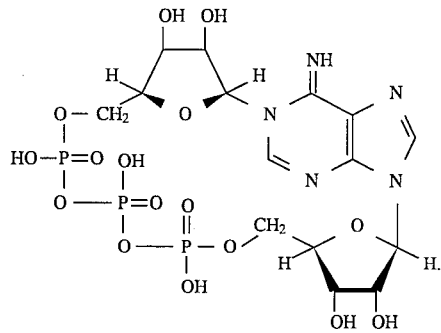

2. A compound having the chemical structure as follows:

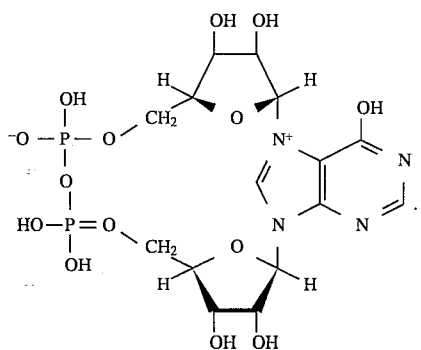

3. A compound having the chemical structure as follows:

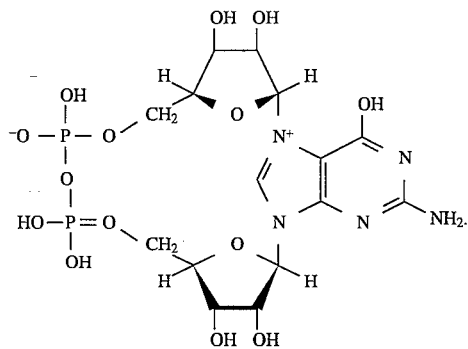

(3)

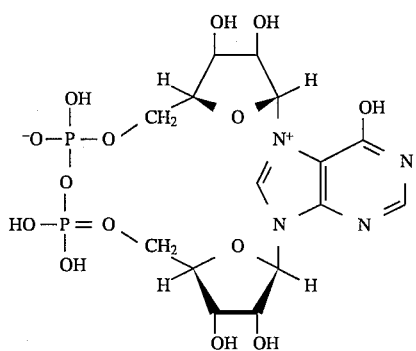

Figure 2:
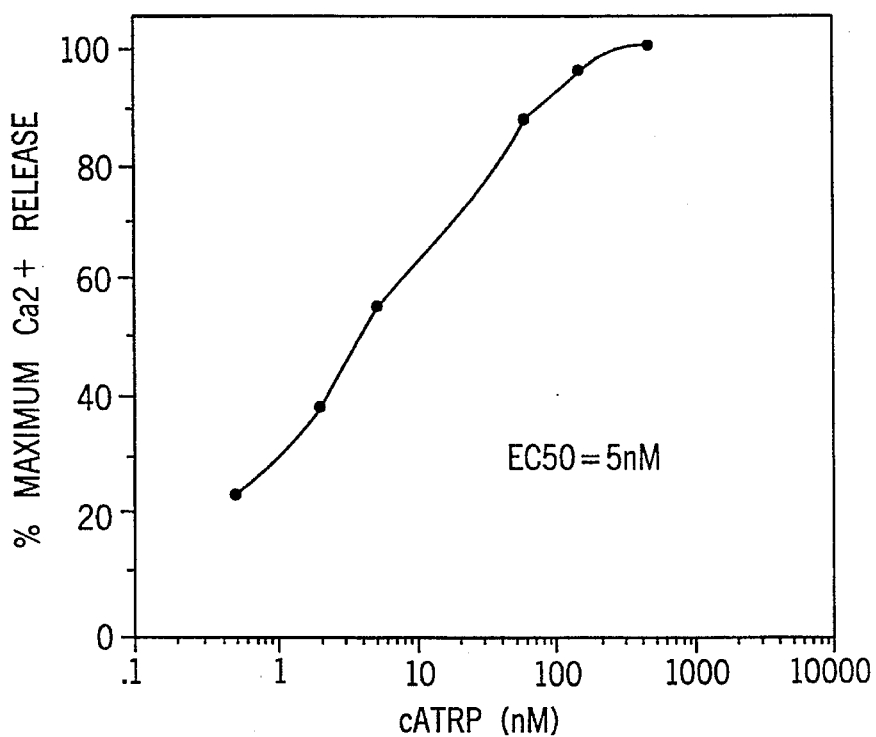
FIG. 2 illustrates the calcium releasing activity of cATPR in rat liver microsomes.

These cADPR homologs were evaluated for their $Ca^{2+}$ releasing activities. It was shown that cATPR also stimulated $Ca^{2+}$ release in rat brain microsomes with an $ED_{50}$ of 5 nM (see FIG. 2), which is approximately 20 times more potent than cADPR ($ED_{50}$=100 nM) in this assay.

$Ca^{2+}$ release measurements were done as outlined in Example 1.

I claim:

1. A compound having the chemical structure as follows:

* * * * *